US012533493B2

United States Patent

(12) United States Patent
Scherich et al.

(10) Patent No.: US 12,533,493 B2
(45) Date of Patent: Jan. 27, 2026

(54) VASCULAR ACCESS INSTRUMENT ADVANCEMENT DEVICES, SYSTEMS, AND METHODS

(71) Applicant: Becton, Dickinson and Company, Franklin Lakes, NJ (US)

(72) Inventors: Megan Scherich, Salt Lake City, UT (US); Weston F. Harding, Lehi, UT (US); Justin G. Hortin, Farmington, UT (US); Bart D. Peterson, Farmington, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 355 days.

(21) Appl. No.: 17/574,127

(22) Filed: Jan. 12, 2022

(65) Prior Publication Data

US 2022/0218955 A1 Jul. 14, 2022

Related U.S. Application Data

(60) Provisional application No. 63/137,049, filed on Jan. 13, 2021.

(51) Int. Cl.
*A61M 25/06* (2006.01)

(52) U.S. Cl.
CPC .... *A61M 25/0606* (2013.01); *A61M 25/0693* (2013.01)

(58) Field of Classification Search
CPC .. A61M 2025/09116; A61M 25/09041; A61M 2025/0037; A61M 25/0693;
(Continued)

(56) References Cited

U.S. PATENT DOCUMENTS 5,356,390 A * 10/1994 Erskine ............. A61M 25/0631 604/249
5,360,417 A 11/1994 Gravener et al.
(Continued)

FOREIGN PATENT DOCUMENTS

JP H07148268 A 6/1995
JP 2003230631 A 8/2003
(Continued)

*Primary Examiner* — Courtney B Fredrickson
*Assistant Examiner* — Kayla M. Turkowski
(74) *Attorney, Agent, or Firm* — The Webb Law Firm

(57) ABSTRACT

A vascular access instrument advancement device may include a housing and an extension tube extending through the housing. The extension tube may extend through the housing. The extension tube may include a first lumen and a second lumen. A blood collection pathway may extend through the first lumen. A wedge may be disposed within the housing and the second lumen of the extension tube. A pair of opposing pinch members may be configured to pinch the extension tube. The pair of opposing pinch members may be disposed within the housing proximal to the wedge and configured to move along the extension tube with the housing. An instrument may extend distally from the wedge. The instrument may be disposed within the second lumen. In response to moving the housing distally along the extension tube, the pair of opposing pinch members push the wedge distally and the instrument is advanced distally.

19 Claims, 10 Drawing Sheets

(58) Field of Classification Search
CPC .... A61M 25/0097; A61M 2025/09125; A61M 2025/0035; A61M 2025/0078; A61M 25/003; A61M 2025/0018; A61M 25/0606; A61M 25/06; A61M 25/065; A61B 2017/22049; A61B 2017/22038
See application file for complete search history.

(56) References Cited

U.S. PATENT DOCUMENTS

| | | | | | |
|---|---|---|---|---|---|
| 5,836,306 | A * | 11/1998 | Duane | A61M 39/0693 600/585 |
| 6,082,827 | A * | 7/2000 | McFall | B65G 47/967 298/7 |
| 6,626,869 | B1 * | 9/2003 | Bint | A61M 25/09041 604/164.01 |
| 2004/0122363 | A1 | 6/2004 | Gribbons et al. | |
| 2004/0260329 | A1 | 12/2004 | Gribbons et al. | |
| 2005/0209582 | A1 * | 9/2005 | Quinn | A61M 25/0053 604/161 |
| 2009/0188531 | A1 * | 7/2009 | Boyle, Jr. | B08B 9/0436 134/146 |
| 2011/0306993 | A1 | 12/2011 | Hull et al. | |
| 2016/0287065 | A1 * | 10/2016 | Ha | A61B 1/00154 |
| 2017/0120014 | A1 * | 5/2017 | Harding | A61M 25/0693 |
| 2017/0216564 | A1 | 8/2017 | Devgon et al. | |
| 2017/0224953 | A1 * | 8/2017 | Tran | A61M 25/0045 |
| 2018/0333560 | A1 * | 11/2018 | Milner | A61M 25/0136 |
| 2019/0060616 | A1 * | 2/2019 | Solomon | A61M 39/1011 |
| 2019/0321590 | A1 * | 10/2019 | Burkholz | A61M 25/09041 |
| 2020/0094016 | A1 * | 3/2020 | Breindel | A61M 25/0009 |
| 2020/0276419 | A1 * | 9/2020 | Franklin | A61M 25/0693 |
| 2020/0316346 | A1 | 10/2020 | Burkholz et al. | |

FOREIGN PATENT DOCUMENTS

| | | | | |
|---|---|---|---|---|
| JP | 2006175070 | A | 7/2006 | |
| JP | 2019509781 | A | 4/2019 | |
| JP | 2020522303 | A | 7/2020 | |
| WO | WO-2013142386 | A1 * | 9/2013 | A61B 17/12031 |
| WO | 2018152059 | A1 | 8/2018 | |
| WO | 2018218236 | A1 | 11/2018 | |
| WO | 2021141774 | A1 | 7/2021 | |
| WO | 2021195054 | A1 | 9/2021 | |

* cited by examiner

VASCULAR ACCESS INSTRUMENT ADVANCEMENT DEVICES, SYSTEMS, AND METHODS

CROSS-REFERENCE TO RELATED APPLICATION

The present application claims priority to U.S. Provisional Application Ser. No. 63/137,049, entitled "Vascular Access Instrument Advancement Devices, Systems, and Methods" filed Jan. 13, 2021, the entire disclosure of which is hereby incorporated by reference in its' entirety.

BACKGROUND

Catheters are commonly used to infuse fluids into vasculature of a patient. For example, catheters may be used for infusing normal saline solution, various medicaments, or total parenteral nutrition. Catheters may also be used for withdrawing blood from the patient.

A catheter may include an over-the-needle peripheral intravenous ("IV") catheter. In this case, the catheter may be mounted over an introducer needle having a sharp distal tip. The catheter and the introducer needle may be assembled so that the distal tip of the introducer needle extends beyond the distal tip of the catheter with the bevel of the needle facing up away from skin of the patient. The catheter and introducer needle are generally inserted at a shallow angle through the skin into vasculature of the patient.

In order to verify proper placement of the introducer needle and/or the catheter in the blood vessel, a clinician generally confirms that there is "flashback" of blood in a flashback chamber. After placement of the introducer needle has been confirmed, the clinician may remove the introducer needle, leaving the catheter in place for future blood withdrawal or fluid infusion.

Overtime the catheter can become occluded at a tip of the catheter due to presence of fibrin sheath, thrombus, or vein walls or valves. Occlusions can limit functionality of the catheter for infusion and/or blood draw. The subject matter claimed herein is not limited to embodiments that solve any disadvantages or that operate only in environments such as those described above. Rather, this background is only provided to illustrate one example technology area where some implementations described herein may be practiced.

SUMMARY OF THE INVENTION

The present disclosure relates generally to an instrument advancement device, as well as related systems and methods. In some embodiments, the instrument advancement device may include a housing and an extension tube extending through the housing. In some embodiments, the extension tube may include a first lumen and a second lumen. It is understood that, in some embodiments, the extension tube may include one or more additional lumens to the first lumen and the second lumen. In some embodiments, a blood collection pathway may extend through the first lumen and/or one or more of the additional lumens.

In some embodiments, the instrument advancement device may include a wedge disposed within the housing and the second lumen of the extension tube. In some embodiments, the instrument advancement device may include a pair of opposing pinch members configured to pinch the extension tube. In some embodiments, the pair of opposing pinch members may be disposed within the housing and configured to move along the extension tube with the housing. In some embodiments, the pair of opposing pinch members may be disposed within the housing proximal to the wedge.

In some embodiments, the instrument advancement device may include an instrument, which may extend distally from the wedge. In some embodiments, the instrument may be disposed within the second lumen. In some embodiments, in response to moving the housing distally along the extension tube, the pair of opposing pinch members may push the wedge distally and the instrument may be advanced distally. In some embodiments, the instrument may include a vascular access instrument configured to advance distally through a catheter assembly and into vasculature of a patient.

In some embodiments, the instrument advancement device may include another pair of opposing pinch members configured to pinch the extension tube. In some embodiments, the other pair of opposing pinch members may be disposed within the housing distal to the wedge and configured to move along the extension tube with the housing. In some embodiments, in response to moving the housing proximally along the extension tube, the other pair of opposing pinch members may push the wedge proximally and the instrument may be retracted proximally.

In some embodiments, in response to movement of the housing along the extension tube, the opposing pinch members may rotate with respect to the housing and the extension tube. In some embodiments, an inner surface of the housing may include one or more bumps in contact with the pair of opposing pinch members. In some embodiments, the opposing pinch members may be fixed with respect to the housing.

In some embodiments, the instrument may include a guidewire. In some embodiments, the instrument advancement device may include a distal adapter. In some embodiments, a distal end of the extension tube may be coupled to the distal adapter. In some embodiments, the instrument advancement device may include a septum disposed within the distal adapter and configured to seal the second lumen and not the first lumen. In some embodiments, the instrument advancement device may include a septum disposed within the distal adapter and sealing the second lumen. In some embodiments, the instrument advancement device may include a blunt cannula, which may extend from the first lumen through the septum.

In some embodiments, the distal adapter may include a shaft and opposing lever locks. In some embodiments, the shaft may include a blunt cannula. In some embodiments, the instrument advancement device may include a cap disposed on the shaft. In some embodiments, a distal end of the cap may include an opening.

In some embodiments, the first lumen may extend through the extension tube. In some embodiments, the second lumen may extend through the extension tube. In some embodiments, a top surface of the extension tube may include a marking. In some embodiments, in response to the housing being aligned with the marking, the instrument may be advanced distally beyond a catheter tip a distance. In some embodiments, the marking may indicate the distance. In some embodiments, the top surface of the extension tube may include another marking. In some embodiments, in response to the housing being aligned with the other marking, the instrument may be aligned with the catheter tip.

In some embodiments, a top surface of the extension tube or distal adapter may include a marking. In some embodiments, the top surface of the instrument may include another marking. In some embodiments, in response to the other marking being aligned with the marking, the instrument may be advanced distally the distance beyond the catheter tip.

In some embodiments, the top surface of the extension tube or distal adapter may include a marking. In some embodiments, the top surface of the instrument may include another marking. In some embodiments, in response to the other marking being aligned with the marking, the instrument may be aligned with the catheter tip.

In some embodiments, the top surface of the distal adapter may include a marking. In some embodiments, the top surface of the instrument may include another marking. In some embodiments, in response to the other marking being moved from a proximal end of the marking to a distal end of the marking, the instrument may be advanced beyond the catheter tip a length of the marking. In some embodiments, the length of the marking may be 10 mm, 20 mm, 30 mm, 40 mm, 50 mm, or another length. In some embodiments, the length of the marking may be between 10 mm and 50 mm, inclusive, between 10 mm and 30 mm, inclusive, between 10 mm and 40 mm, inclusive, or between 20 mm and 40 mm, inclusive, for example.

In some embodiments, the instrument delivery device may include a proximal adapter coupled to a proximal end of the extension tube. In some embodiments, the proximal adapter may be configured to couple to a blood collection device. In some embodiments, the distal adapter and/or the proximal adapter may overmolded onto the extension tube, which may prevent fluid leakage.

It is to be understood that both the foregoing general description and the following detailed description are examples and explanatory and are not restrictive of the invention, as claimed. It should be understood that the various embodiments are not limited to the arrangements and instrumentality illustrated in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE DRAWINGS

Example embodiments will be described and explained with additional specificity and detail through the use of the accompanying drawings in which.

DESCRIPTION OF EMBODIMENTS

Figure 1:
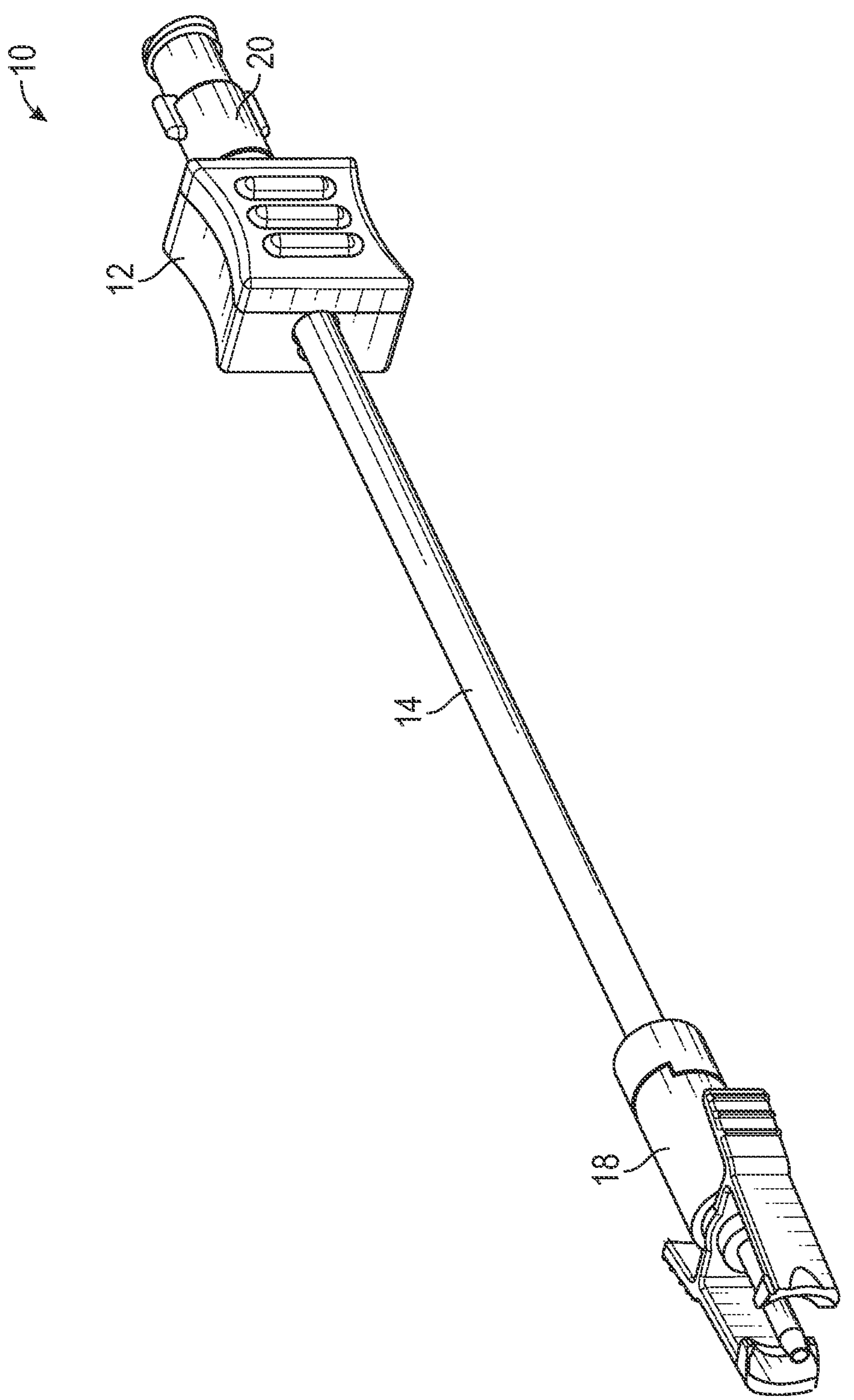
FIG. 1 is an upper perspective view of an example instrument advancement device, according to some embodiments.

Referring now to FIG. 1, an instrument advancement device 10 is illustrated, according to some embodiments. In some embodiments, the instrument advancement device 10 may include a housing 12 and an extension tube 14 extending through the housing 12. In some embodiments, the extension tube 14 may be rigid, semi-rigid, or flexible. In some embodiments, the extension tube 14 may include a coextruded guidewire to add stiffness to the extension tube 14. In some embodiments, the extension tube 14 may include a multi-lumen extension tube.

In some embodiments, the instrument advancement device 10 may include an instrument 16, which may include a guidewire, a tube, or another suitable instrument. In some embodiments, the instrument 16 may be colored to increase visibility. In some embodiments, the guidewire may be constructed of metal or another suitable material. In these and other embodiments, the instrument 16 may be lubricated or coated to ease advancement. In some embodiments, the tube may be soft or stiff. In some embodiments, the tube may create a closed path for blood flow and/or reduce contamination of the blood due to drug adsorption in a catheter assembly.

In some embodiments, the instrument 16 may include a guidewire, which may include a spring or coil. In some embodiments, the spring or coil may include varying pitches along a length of the spring or coil. For example, a pitch of the spring or coil upstream from or proximal to a catheter tip may be larger to facilitate more blood flow and increase flow rate, and a pitch of the spring or coil near the catheter tip may be smaller to prevent blood clots from entering the catheter tip, while still allowing blood to flow through it. In some embodiments, the guidewire may include a rod, which may extend through a center portion of the spring or coil. In some embodiments, the guidewire may include the rod and may not include the spring or coil.

Over time a catheter can become occluded at the catheter tip due to presence of fibrin sheath, thrombus, or vein walls or valves. In some embodiments, the instrument 16 may be configured to extend into and/or through the catheter assembly to push through and/or disrupt an occlusion of the catheter. In some embodiments, the instrument 16 may overcome thrombus and fibrin sheath in or around the catheter assembly or in the vein that might otherwise prevent blood draw. In some embodiments, the instrument advancement device 10 may reduce trauma to the vasculature while also facilitating fluid delivery, blood collection, patient or device monitoring, or other clinical needs. In some embodiments, the instrument advancement device 10 may decrease hemolysis and reduce blood exposure. In some embodiments, the instrument 16 may include a vascular access instrument configured to advance distally through the catheter assembly and into the vasculature of the patient.

In some embodiments, a distal end of the instrument advancement device 10 may include a distal adapter 18 or another suitable connector. In some embodiments, the distal adapter 18 may be configured to couple to the catheter assembly, which may be existing or already dwelling within the vasculature of the patient. In some embodiments, the catheter assembly may include a catheter adapter, which may include a distal end, a proximal end, and a lumen extending through the distal end of the catheter adapter and the proximal end of the catheter adapter. In some embodiments, the catheter may extend from the distal end of the catheter adapter. In some embodiments, the catheter may include a peripheral intravenous catheter, a midline catheter, or a peripherally inserted central catheter. In some embodiments, the catheter assembly may include an introducer needle, which may extend through the catheter and facilitate piercing of skin and the vasculature to insert the catheter into the patient. In some embodiments, the introducer needle may be removed from the catheter assembly prior to coupling of the instrument advancement device 10 to the catheter assembly.

In some embodiments, the catheter assembly may be straight. In other embodiments, the catheter assembly may be integrated, having an extension tube that is integrated with the catheter adapter. In some embodiments, the catheter assembly may include an extension set, which may include the extension tube extending from and integrated with a side port of the catheter adapter. In some embodiments, the distal adapter 18 may be configured to couple to a portion of the catheter assembly, such as the proximal end of the catheter adapter and/or a needleless access connector. In some embodiments, the needleless access connector may be coupled to a proximal end, a T-connector, or another portion of the extension set. In some embodiments, the needleless access connector may be permanently connected, such as, for example, via adhesive, to the distal adapter 18 to prevent intentional or unintentional removal by a user.

In some embodiments, a distal end of the extension tube 14 may be coupled to the distal adapter 18. In some embodiments, a proximal end of the extension tube 14 may be coupled to a proximal adapter 20, which may include another distal adapter or another suitable connector. In some embodiments, the proximal adapter 20 may be configured to couple to a blood collection device. In some embodiments, the blood collection device may include a syringe, a BD VACUTAINER® one-use holder (available from Becton, Dickinson and Company of Franklin Lakes, New Jersey), a BD VACUTAINER® LUER-LOK™ access device (also available from Becton, Dickinson and Company of Franklin Lakes, New Jersey), or another suitable blood collection device, which may provide suction.

In some embodiments, the instrument 16 may be advanced prior to or during infusion or blood draw. In some embodiments, after completing a blood draw or infusion and before uncoupling the instrument advancement device 10 from the catheter assembly, the user may retract the instrument by moving the housing 12 backward or proximally. Thus, in some embodiments, a risk of exposure of the user to blood may be decreased.

Figure 2:
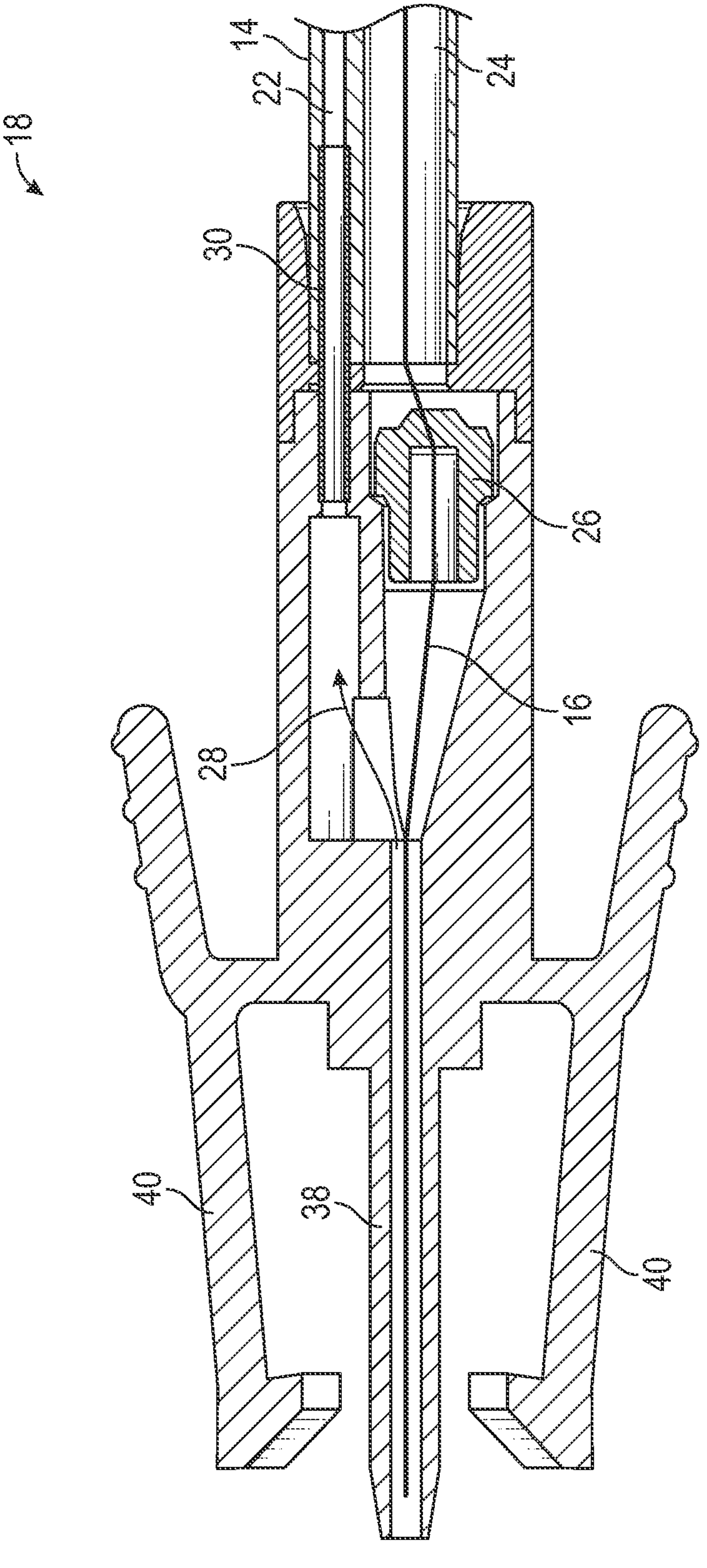
FIG. 2 is a cross-sectional view of an example distal end of the instrument advancement device, according to some embodiments.

Referring now to FIG. 2, in some embodiments, the extension tube 14 may include a first lumen 22 and a second lumen 24, which may be separate from the first lumen 22 along an entire length of the extension tube 14. In some embodiments, a blood collection pathway may extend through the first lumen 22. In some embodiments, the instrument 16 may be disposed within the second lumen 24. In some embodiments, a diameter of the second lumen 24 may be larger than a diameter of the first lumen 22. In some embodiments, the diameter and/or a length of the first lumen 22 may be selected based on a desired flow rate and/or to reduce hemolysis.

In some embodiments, in response to moving the housing 12 distally along the extension tube 14, the instrument 16 may be advanced distally within the second lumen 24. In some embodiments, in response to moving the housing 12 proximally along the extension tube 14, the instrument 16 may be retracted proximally within the second lumen 24.

In some embodiments, the instrument advancement device 10 may include a septum 26 disposed within the distal adapter 18 and configured to seal the second lumen 24 or prevent blood flow into the second lumen 24. In these and other embodiments, the septum 26 may not seal the first lumen 22 such that blood may flow proximally along a fluid pathway 28 from the distal adapter 18 through the first lumen 22 for blood collection. In some embodiments, the septum 26 may be elastomeric.

In some embodiments, a distal end of the instrument 16 may be disposed proximal to a distal end of the distal adapter 18 when the housing 12 is fully retracted in a proximal direction. In some embodiments, the distal end of the instrument 16 may be disposed proximal to the septum 26 when the housing 12 is fully retracted in the proximal direction and/or the instrument 16 may be sealed within the extension tube 14.

In some embodiments, the instrument advancement device 10 may include a cannula 30, which may connect a distal end of the first lumen 22 and the distal adapter 18. In some embodiments, the cannula 30 may be blunt. In some embodiments, the fluid pathway 28 may extend through the cannula 30, which may prevent blood leakage. In some embodiments, the cannula 30 may be constructed of steel, plastic, metal, or another suitable material. In some embodiments, the cannula 30 may be coupled to the distal adapter 18 or monolithically formed with the distal adapter 18 as a single unit. In some embodiments, the septum 26 may be concentric with the second lumen 24 or offset slightly to obtain adequate wall thicknesses.

In some embodiments, the distal adapter 18 may include a shaft 38 and opposing lever locks 40. In some embodiments, the lever locks 40 may facilitate coupling to the needleless access connector. In some embodiments, the shaft 38 may be lubricated with a lubricant, which may reduce a force of insertion into the catheter assembly. In some embodiments, the male distal adapter may include a male luer, a male luer lock, a male slip luer, a luer, or another suitable connector.

Figure 3:
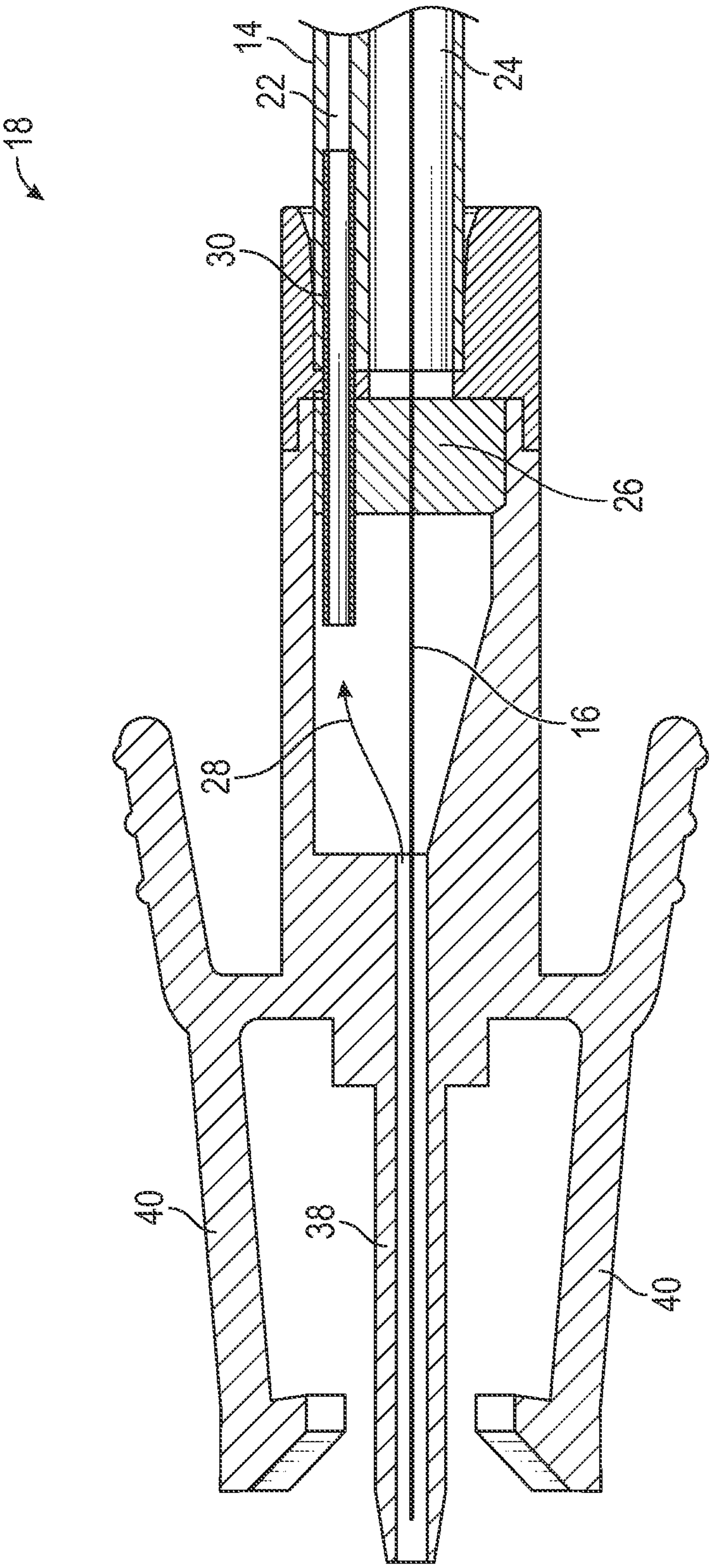
FIG. 3 is a cross-sectional view of another example distal end of the instrument advancement device, according to some embodiments.

Referring now to FIG. 3, in some embodiments, the septum 26 may extend across a width of an inner lumen of the distal adapter 18. In some embodiments, the septum 26 may seal the second lumen 24 or prevent blood flow into the second lumen 24. In some embodiments, the cannula 30 may extend from the first lumen 22 through the septum 26 to allow fluid flow therethrough.

Figure 4:
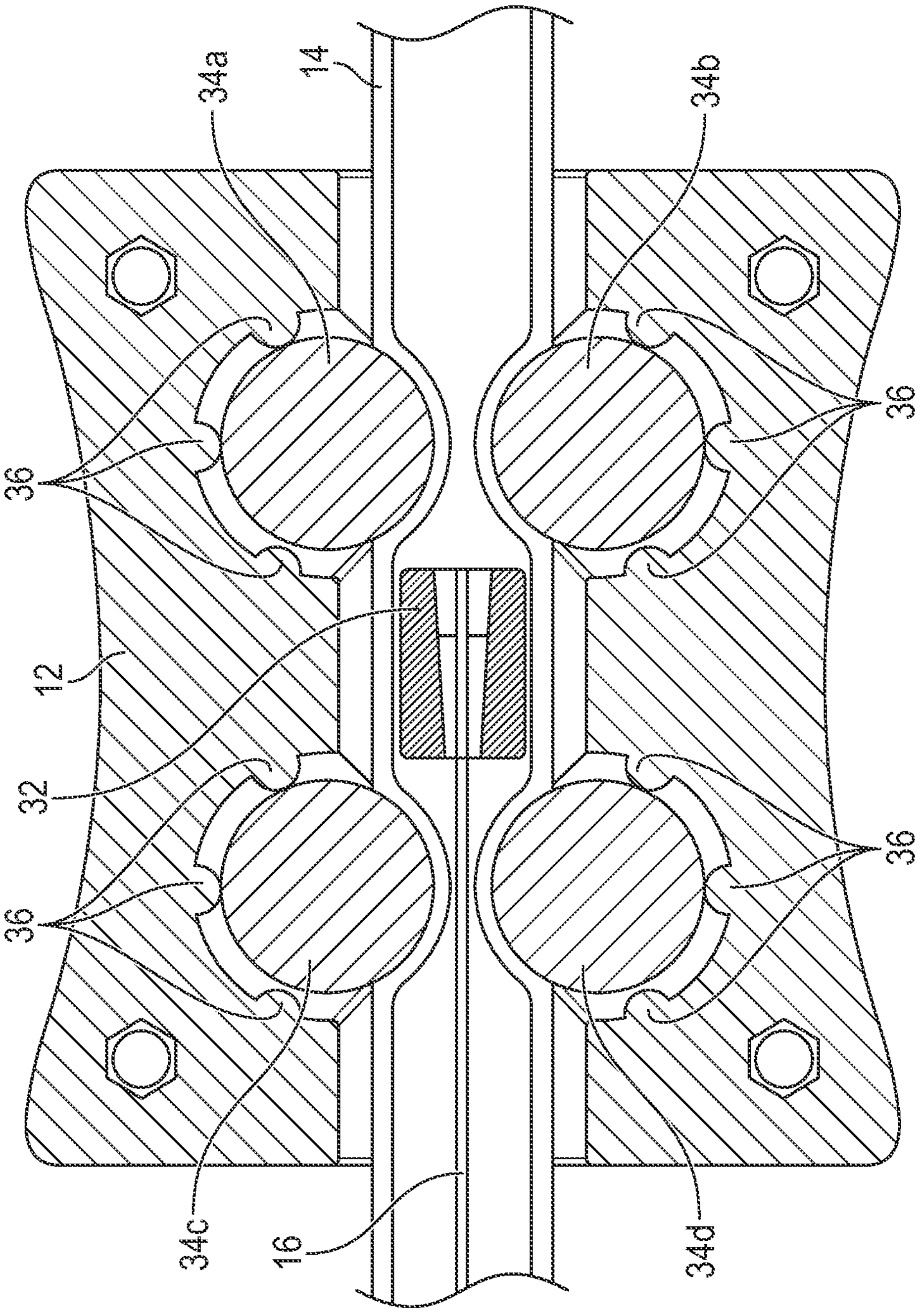
FIG. 4 is a cross-sectional view of an example housing of the instrument advancement device, illustrating an example extension tube extending therethrough, according to some embodiments.

Referring now to FIG. 4, in some embodiments, the instrument advancement device 10 may include a wedge 32 disposed within the housing 12 and the second lumen 24 of the extension tube 14. In some embodiments, the instrument advancement device 10 may include a pair of opposing pinch members 34 configured to pinch the extension tube 14. In some embodiments, the pair of opposing pinch members 34*a,b* may be disposed within the housing 12 proximal to the wedge 32 and configured to move along the extension tube 14 with the housing 12.

In some embodiments, the instrument 16 may extend distally from the wedge 32. In some embodiments, the instrument 16 may be disposed within the second lumen 24. In some embodiments, in response to moving the housing 12 distally along the extension tube 14, the pair of opposing pinch members 34*a,b* may push the wedge 32 distally, and the instrument 16 may be advanced distally.

In some embodiments, the instrument advancement device 10 may include another pair of opposing pinch members 34*c,d* configured to pinch the extension tube 14. In some embodiments, the other pair of opposing pinch members 34*c,d* may be disposed within the housing distal to the wedge 32 and configured to move along the extension tube 14 with the housing 12. In some embodiments, in response to moving the housing 12 proximally along the extension tube 14, the pair of opposing pinch members 34*c,d* may push the wedge 32 proximally and the instrument 16 may be retracted proximally.

The pair of opposing pinch members 34*a,b* and the other pair of opposing pinch members 34*c,d* may be referred to collectively in the present disclosure as "opposing pinch members 34." In some embodiments, in response to movement of the housing 12 along the extension tube 14, the opposing pinch members 34 may rotate with respect to the housing 12 and the extension tube 14. In some embodiments, in response to movement of the housing 12 along the extension tube 14, the opposing pinch members 34 may rotate with respect to the housing 12 and the extension tube 14, which may rotate the instrument 16. In some embodiments, an inner surface of the housing 12 may include one or more bumps 36 in contact with the opposing pinch members 34, which may reduce friction as the opposing pinch members 34 rotate. In some embodiments, the wedge 32 and/or the opposing pinch members 34 may be lubricated with a lubricant, which may reduce friction.

In some embodiments, the opposing pinch members 34 may be constructed of plastic, metal, or another suitable material. In some embodiments, the opposing pinch members 34 may include spherical balls, ball bearings, wheels, or cylinders, which may be configured to rotate with respect to the housing 12. In some embodiments, the opposing pinch members 34 may include the wheels, which may be smooth or include feet along their edges. In these embodiments, lubricant may be applied to axels of the wheels to reduce friction. In some embodiments, the opposing pinch members 34 may be fixed with respect to the housing 12. For example, the opposing pinch members 34 may be molded into the housing 12.

In some embodiments, a number of the opposing pinch members 34 may vary based on a shape of the wedge 32. In some embodiments, the instrument advancement device 10 may include the pair of opposing pinch members 34*a,b* and the other pair of opposing pinch members 34*c,d* in response to the shape of the wedge 32 being cylindrical, for example. In some embodiments, the instrument advancement device 10 may include a single pair of the opposing pinch members 34, such as the pair of the opposing pinch members 34*a,b*, in response to the wedge 12 including a dog bone shape, and the single pair may be disposed in a middle or depression of the dog bone shape.

Figure 5A:
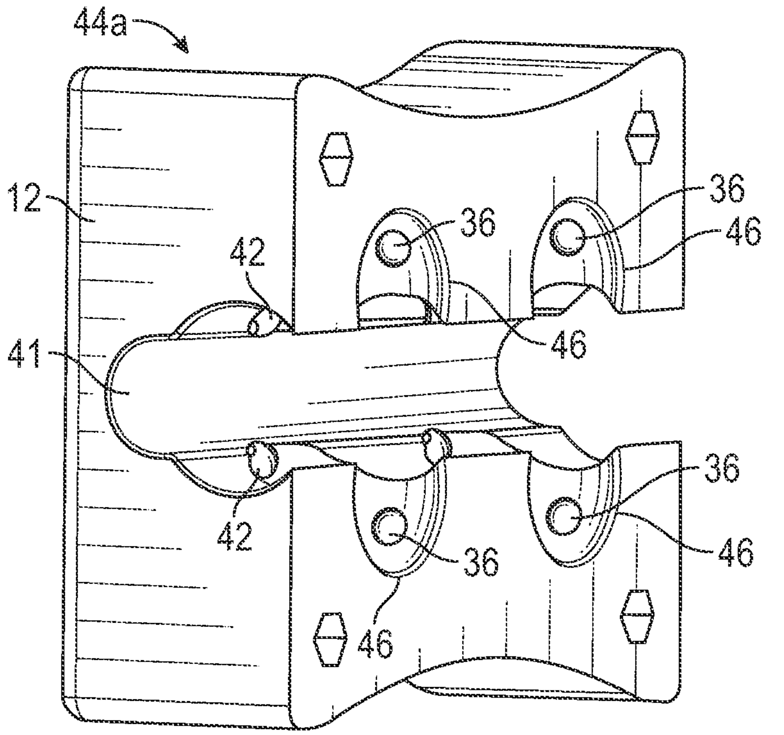
FIG. 5A is an upper perspective view of an example piece of the housing, according to some embodiments.
Figure 5B:
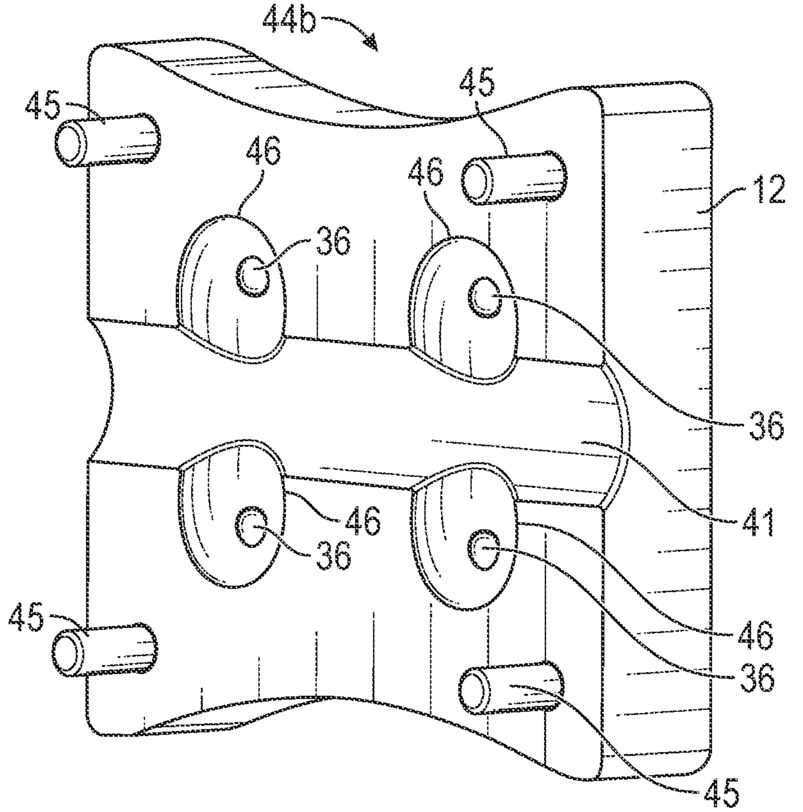
FIG. 5B is an upper perspective view of another example piece of the housing configured to couple to the piece of the housing of FIG. 5A, according to some embodiments.

Referring now to FIG. 5A-5B, in some embodiments, the housing 12 may include an aperture 41 extending therethrough and configured to receive the extension tube 14. In some embodiments, the inner surface of the housing 12 may include one or more protrusions 42, which may contact the extension tube 14 to reduce friction between the extension tube 14 and the housing 12 as the housing 12 moves along the extension tube 14. In some embodiments, the housing 12 may include multiple pieces 44*a,b*, which may be coupled together via pegs 45 or any other suitable mechanism. In other embodiments, the housing 12 may be monolithically formed as a single unit.

In some embodiments, the housing 12 may include multiple cutouts 46, which may include the bumps 36. In these and other embodiments, the opposing pinch members 34 may include the spherical balls. In some embodiments, the cutouts 46 may be generally spherical and/or may extend outwardly from the aperture 41. In some embodiments, halves of the cutouts 46 illustrated in the multiple pieces 44*a,b* may be joined together to form the cutouts 46.

In some embodiments, the housing 12 may be rigid or semi-rigid to facilitate gripping and/or one-handed advancement by the user. In some embodiments, the housing 12 may include one or more grip features or a shape to facilitate gripping by the user. In some embodiments, the grip features may include one or more of ridges, indents, and tabs on a top of the housing 12 and/or one or more sides of the housing 12. In some embodiments, the shape of the housing 12 may include a square, cylinder, dog bone, or another suitable shape. In some embodiments, the shape of the housing 12 and/or the grip features may facilitate the user advancing and/or retracting the instrument 16 without contacting the instrument, thereby decreasing a risk of contamination and/or infection. In some embodiments, the housing 12 may include one or more textured surfaces to facilitate gripping by the user.

Figure 6A:
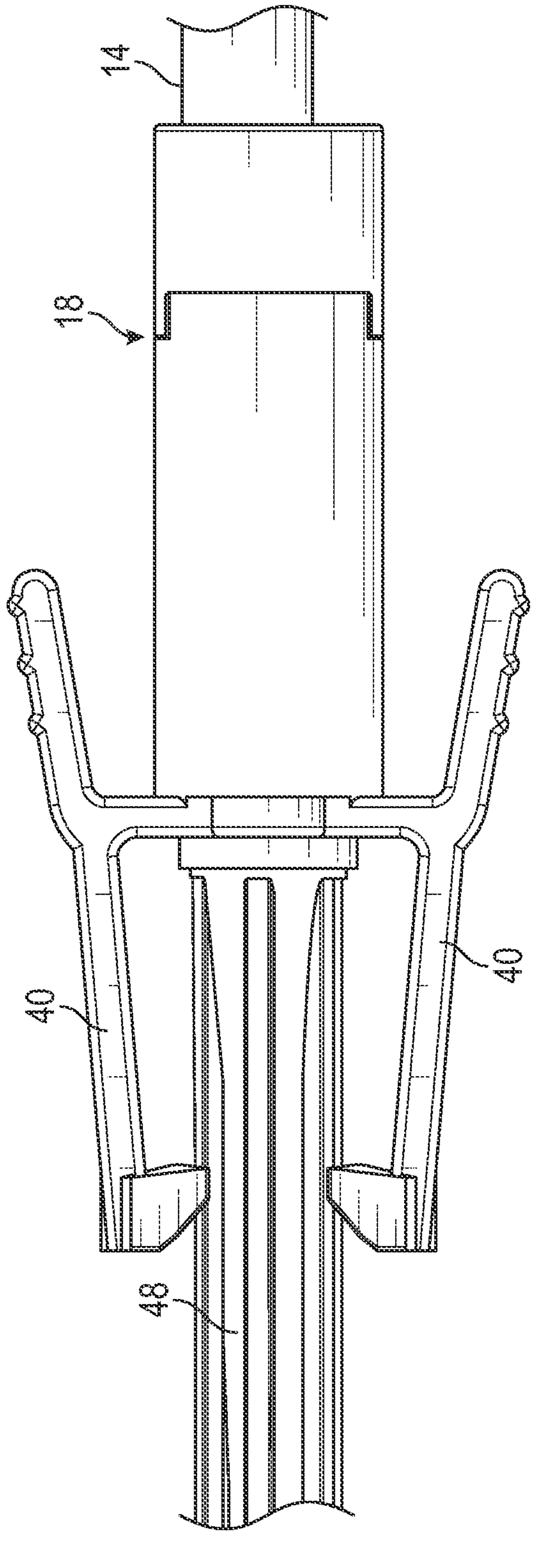
FIG. 6A is a top view of an example cap coupled to the instrument advancement device, according to some embodiments.
Figure 6B:
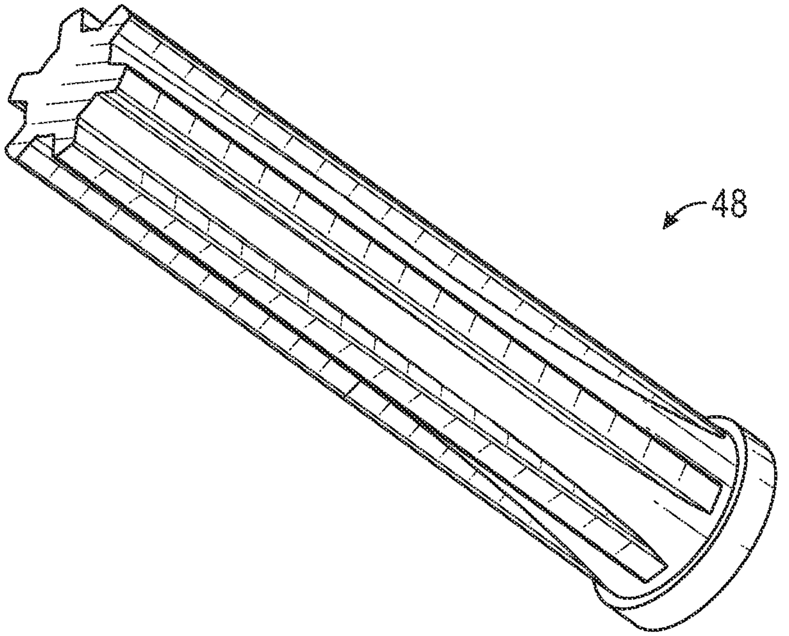
FIG. 6B is an upper perspective view of the cap, according to some embodiments.
Figure 6C:
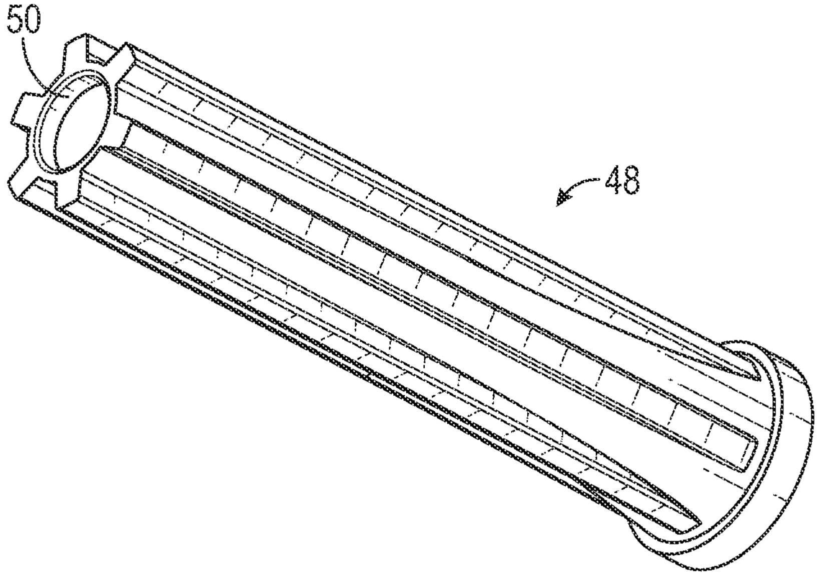
FIG. 6C is another upper perspective view of the cap, illustrating an example opening, according to some embodiments.

Referring now to FIG. 6A-6C, in some embodiments, the instrument advancement device 10 may include a cap 48 disposed on the shaft 38. In some embodiments, the cap 48 may include one or more grip features along edges of the cap 48 to ease removal from the shaft 38, which may be blunt. In some embodiments, the cap 48 may be filled in at the distal end, as illustrated, for example, in FIG. 6B, which may prevent the instrument from prematurely pushing past a tip of the shaft 38 during shipping or priming of the instrument advancement device 10.

In some embodiments, a distal end of the cap 48 may include an opening 50, as illustrated, for example, in FIG. 6C. In some embodiments, the opening 50 may reduce material, cost, and prevent damage to the instrument 16 if the user neglects to take off the cap 48 prior to advancement.

Figure 7:
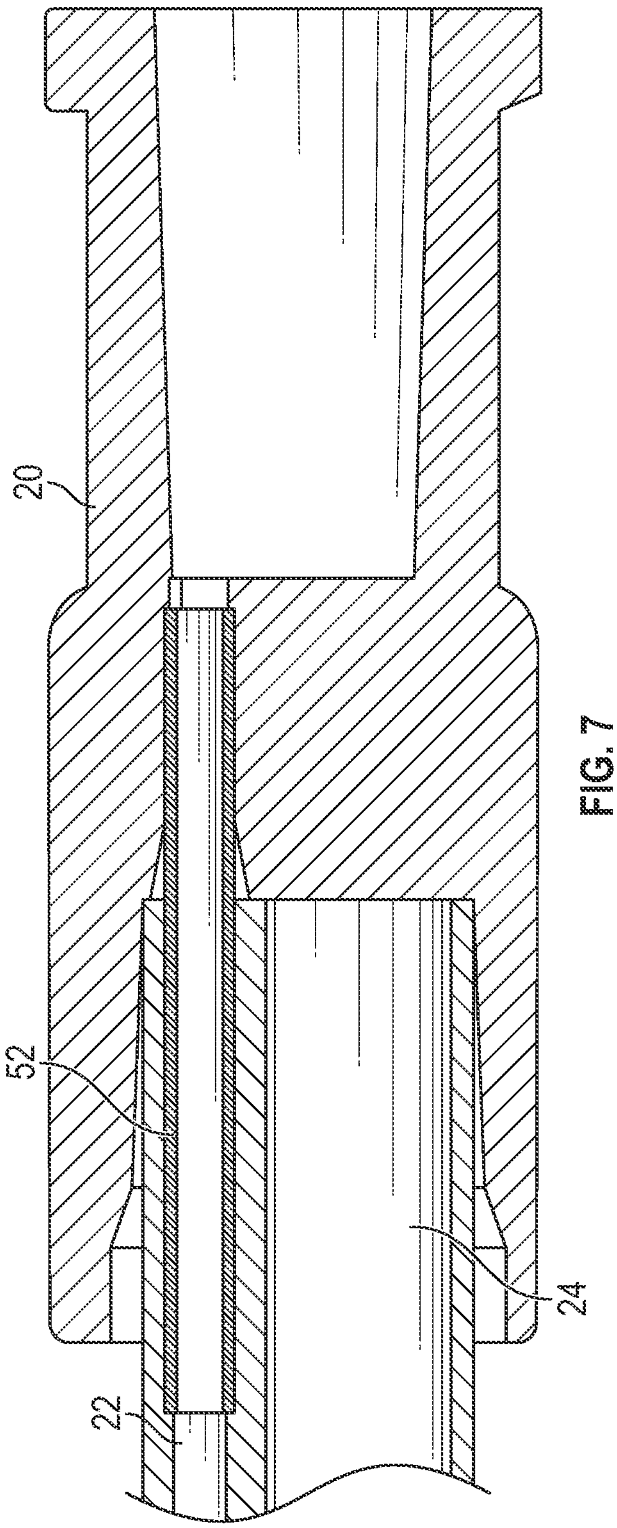
FIG. 7 is a cross-sectional view of an example proximal end of the instrument advancement device, according to some embodiments.

Referring now to FIG. 7, in some embodiments, the proximal end of the extension tube 14 may be coupled to the proximal adapter 20, which may include a female luer, a female luer lock, a female slip luer, a luer, or another suitable connector. In some embodiments, the proximal adapter 20 may be configured to couple to the blood collection device. In some embodiments, the first lumen 22 may extend through the extension tube 14. In some embodiments, the second lumen 24 may extend through the extension tube 14.

In some embodiments, the distal adapter 18 may not include a septum, such as the septum 26 described with respect to FIGS. 2-3. In these and other embodiments, the proximal adapter 20 may block a proximal end of the extension tube 14 to prevent blood leakage through the proximal adapter 20, as illustrated, for example, in FIG. 7. In some embodiments, sealing may be accomplished by over molding the proximal adapter 20 and/or the distal adapter 18 on either end of the extension tube 14 to form a seal around the instrument 16.

In some embodiments, the instrument advancement device 10 may include a cannula 52, which may connect a proximal end of the first lumen 22 and the proximal adapter 20, to prevent blood leakage. In some embodiments, the cannula 52 may be blunt. In some embodiments, the fluid pathway 28 may extend through the cannula 52. In some embodiments, a fluid path, such as a length and/or diameter, through one or more of the following may be selected or optimized to increase a flow rate and decrease a risk of hemolysis: the distal adapter 18, the proximal adapter 20, the cannula 52, the cannula 30, and the extension tube 14.

Figure 8A:
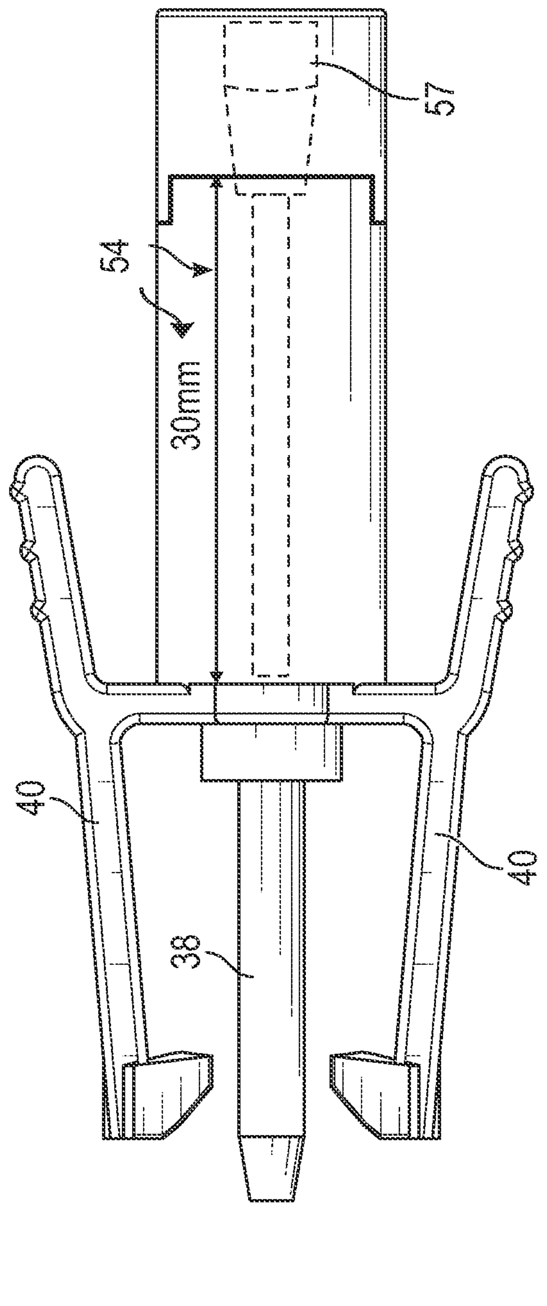
FIG. 8A is a top view of an example distal adapter that includes an example marking, according to some embodiments.
Figure 8B:
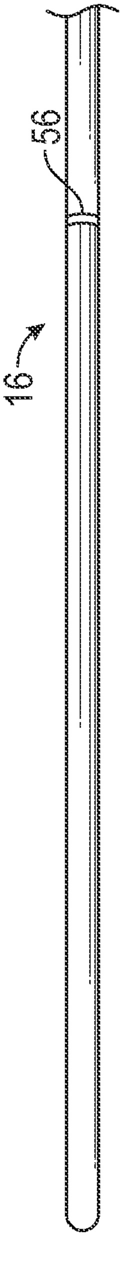
FIG. 8B is an upper perspective view of an example instrument, illustrating another example marking, according to some embodiments.

Referring now to FIGS. 8A-8B, in some embodiments, a top surface of the distal adapter 18 may include a marking 54, which may be visible to the user during use. In some embodiments, a top surface of the instrument 16 may include another marking 56. In some embodiments, the distal adapter 18 may be transparent, which may allow the user to see the other marking 56 through the distal adapter 18. In some embodiments, the marking 54 and/or the other marking 56 may instruct the user about advancement of the instrument 16. In some embodiments, in response to the other marking 56 being moved from a proximal end of the marking 54 to a distal end of the marking 54, the instrument 16 may be advanced beyond the catheter tip a distance equal to a length of the marking 54. In some embodiments, the length of the marking 54 may be 30 mm or another suitable length.

In some embodiments, the marking 54 and/or the other marking 56 may be molded in, etched on, lasered, painted, or provided in another suitable manner. In some embodiments, the marking 54 may include a line that is parallel to a longitudinal axis of the instrument advancement device 10. Additionally, in some embodiments, the marking 54 may include a number and/or units corresponding to the length of marking 54. In some embodiments, the other marking 56 may include a line, which may be perpendicular to the longitudinal axis of the instrument advancement device 10, or another suitable marking. In some embodiments, the instrument 16 may be shaded or frosted, which may facilitate visibility of the instrument 16 by the user. In some embodiments, the distal adapter 18 may include a bond pocket 57 in which the distal end of the extension tube 14 may be secured and/or adhered.

Figure 8C:
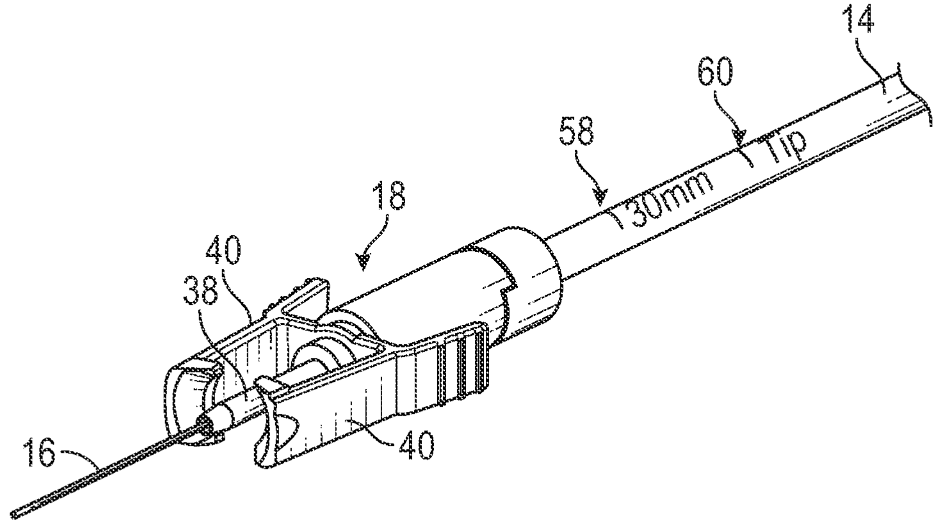
FIG. 8C is an upper perspective view of a portion of the instrument advancement device, illustrating example markings, according to some embodiments.

Referring now to FIG. 8C, in some embodiments, a top surface of the extension tube may include one or more markings, which may be visible to the user during use. In some embodiments, the markings may be molded in, etched on, lasered, painted, or provided in another suitable manner. In some embodiments, the markings may instruct the user about advancement of the instrument 16. In some embodiments, the top surface of the extension tube 14 may include the marking 54 described with respect to FIG. 8A. In some embodiments, in response to the other marking 56 of the instrument (see, for example, FIG. 8B) being moved from a proximal end of the marking 54 to a distal end of the marking 54, the instrument 16 may be advanced beyond the catheter tip a distance equal to a length of the marking 54. In some embodiments, the length of the marking 54 may be 30 mm or another suitable length.

In some embodiments, the markings on the top surface of the extension tube 14 may include a marking 58 and/or a marking 60. In some embodiments, in response to the housing 12 or the marking 56 being aligned with the marking 58, the instrument 16 may be advanced distally beyond the catheter tip 64 of a catheter 62 a distance (see, for example, FIG. 8D). In some embodiments, the marking 58 may indicate the distance, such as, for example 30 mm. In further detail, in some embodiments, the marking 58 may include a number and/or units corresponding to the distance.

In some embodiments, in response to the housing 12 or the marking 56 being aligned with the marking 60, the instrument 16 may be aligned with the catheter tip 64. In some embodiments, the marking 58 and/or the marking 60 may include lines, which may be perpendicular to the longitudinal axis of the instrument advancement device 10, or other suitable markings. In some embodiments, the marking 60 may include a number and/or units corresponding to a position of a distal end of the instrument 16.

Figure 8D:
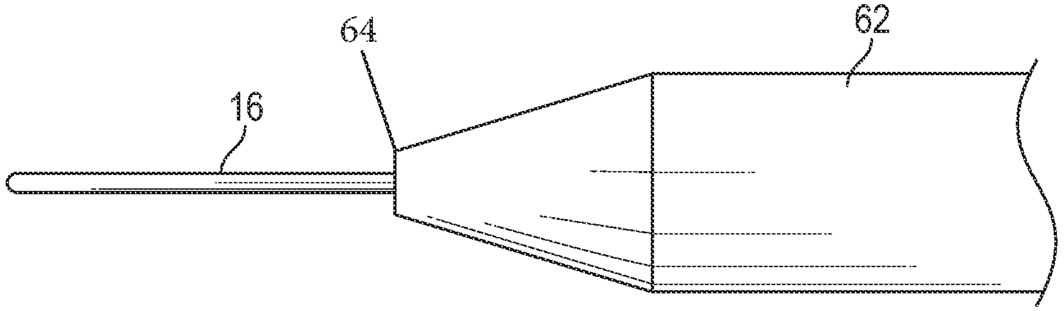
FIG. 8D is an upper perspective view of the instrument advanced distally beyond a catheter tip of an example catheter, according to some embodiments.

In some embodiments, the extension tube 14 may be transparent to facilitate visibility of the instrument 16 therein. In some embodiments, the marking 58 and/or the marking 60 may be disposed on the distal adapter 18, which may be transparent. Referring now to FIG. 8D, the instrument 16 may be disposed distal to the catheter tip 64. In some embodiments, the instrument 16 may be advanced distally beyond the catheter tip 64 in response to the housing 12 being advanced in the distal direction.

All examples and conditional language recited herein are intended for pedagogical objects to aid the reader in understanding the invention and the concepts contributed by the inventor to furthering the art and are to be construed as being without limitation to such specifically recited examples and conditions. Although embodiments of the present inventions have been described in detail, it should be understood that the various changes, substitutions, and alterations could be made hereto without departing from the spirit and scope of the invention.

What is claimed is:

1. A vascular access instrument advancement device, comprising:

a housing;

an extension tube extending through the housing, wherein the extension tube comprises a first lumen and a second lumen each extending from a proximal end of the extension tube to a distal end of the extension tube, wherein a blood collection pathway extends through the first lumen;

a wedge disposed within the housing and the second lumen of the extension tube;

a pair of opposing pinch members configured to pinch the extension tube, wherein the pair of opposing pinch members are disposed within the housing and configured to move along the extension tube with the housing; and an instrument extending distally from the wedge, wherein the instrument is disposed within the second lumen, wherein in response to moving the housing distally along the extension tube, the pair of opposing pinch members push the wedge distally and the instrument is advanced distally through the second lumen, wherein the instrument does not extend through the first lumen.

2. The vascular access instrument advancement device of claim 1, wherein the pair of opposing pinch members are disposed within the housing proximal to the wedge, further comprising a second pair of opposing pinch members configured to pinch the extension tube, wherein the second pair of opposing pinch members are disposed within the housing distal to the wedge and configured to move along the extension tube with the housing, wherein in response to moving the housing proximally along the extension tube, the second pair of opposing pinch members push the wedge proximally and the instrument is retracted proximally.

3. The vascular access instrument advancement device of claim 1, wherein in response to movement of the housing along the extension tube, the pair of opposing pinch members rotate with respect to the housing and the extension tube.

4. The vascular access instrument advancement device of claim 3, wherein an inner surface of the housing comprises a plurality of bumps in contact with the pair of opposing pinch members.

5. The vascular access instrument advancement device of claim 1, wherein the pair of opposing pinch members are fixed with respect to the housing.

6. The vascular access instrument advancement device of claim 1, wherein the instrument comprises a guidewire.

7. The vascular access instrument advancement device of claim 1, further comprising a distal adapter, wherein the distal end of the extension tube is coupled to the distal adapter.

8. The vascular access instrument advancement device of claim 7, further comprising a septum disposed within the distal adapter and configured to seal the second lumen and not the first lumen.

9. The vascular access instrument device of claim 7, further comprising a septum disposed within the distal adapter and sealing the second lumen, further comprising a blunt cannula extending from the first lumen through the septum.

10. The vascular access instrument advancement device of claim 7, wherein the distal adapter comprises a shaft and opposing lever locks, further comprising a cap disposed on the shaft.

11. The vascular access instrument advancement device of claim 7, further comprising a proximal adapter coupled to the proximal end of the extension tube, wherein the distal adapter or the proximal adapter is overmolded onto the extension tube.

12. The vascular access instrument advancement device of claim 7, wherein a top surface of the extension tube or distal adapter comprises a first marking, wherein a top surface of the instrument comprises a second marking, wherein in response to the second marking being aligned with the first marking, the instrument is advanced distally beyond a catheter tip a distance.

13. The vascular access instrument advancement device of claim 7, wherein a top surface of the extension tube or distal adapter comprises a first marking, wherein a top surface of the instrument comprises a second marking, wherein in response to the second marking being aligned with the first marking, the instrument is aligned with a catheter tip.

14. The vascular access instrument advancement device of claim 7, wherein a top surface of the distal adapter comprises a first marking, wherein a top surface of the instrument comprises a second marking, wherein in response to the second marking being moved from a proximal end of the first marking to a distal end of the first marking, the instrument is advanced beyond a catheter tip a distance equal to a length of the first marking.

15. The vascular access instrument advancement device of claim 14, wherein the length of the first marking is between 10 mm and 50 mm, inclusive.

16. The vascular access instrument advancement device of claim 1, wherein a top surface of the extension tube comprises a marking, wherein in response to the housing being aligned with the marking, the instrument is advanced distally beyond a catheter tip a distance.

17. The vascular access instrument advancement device of claim 16, wherein the marking indicates the distance.

18. The vascular access instrument advancement device of claim 16, wherein a top surface of the extension tube comprises a second marking, wherein in response to the housing being aligned with the second marking, the instrument is aligned with the catheter tip.

19. The vascular access instrument advancement device of claim 1, further comprising a proximal adapter coupled to the proximal end of the extension tube, wherein the proximal adapter is configured to couple to a blood collection device.

* * * * *